US005411977A

United States Patent [19]

Petraitis et al.

[11] Patent Number: 5,411,977

[45] Date of Patent: May 2, 1995

[54] SUBSTITUTED 2,5-DIARYL-4-ISOTHIAZOLIN-3-ONES AS ANTIINFLAMMATORY AND ANTITHROMBOTIC AGENTS

[75] Inventors: Joseph J. Petraitis, Glenmoore, Pa.; Susan R. Sherk, Newark, Del.

[73] Assignee: The Dupont Merck Pharmaceutical Company, Wilmington, Del.

[21] Appl. No.: 40,771

[22] Filed: Mar. 31, 1993

[51] Int. Cl.[6] .................. A61K 31/425; C07D 275/02; C07D 275/03

[52] U.S. Cl. ...................................... 514/372; 548/213

[58] Field of Search .......................... 548/213; 514/372

[56] References Cited

U.S. PATENT DOCUMENTS

| | | | |
|---|---|---|---|
| 4,490,462 | 12/1984 | Kawaguchi et al. | 430/543 |
| 5,210,094 | 5/1993 | Reeve | 514/372 |
| 5,342,836 | 8/1994 | Reeve | 514/242 |

*Primary Examiner*—Mary C. Lee
*Assistant Examiner*—Michael G. Ambrose

[57] ABSTRACT

The present invention relates to substituted 2, 5-diaryl-4-isothiazolin-3-ones, pharmaceutical preparations containing them, and their use in the treatment of, thrombosis and, especially inflammation.

4 Claims, No Drawings

SUBSTITUTED 2,5-DIARYL-4-ISOTHIAZOLIN-3-ONES AS ANTIINFLAMMATORY AND ANTITHROMBOTIC AGENTS

BACKGROUND

FIELD OF THE INVENTION

The present invention relates to substituted 2,5-diaryl-4-isothiazolin-3-ones, processes for their manufacture, pharmaceutical preparations containing them, and their use in the treatment of, thrombosis and, especially inflammation.

Inflammatory diseases are a widespread cause of human suffering and loss of function. Additionally, the treatment of patients with these diseases represents a very large expense in terms of money, facilities and personnel. The incidence of many such diseases is expected to rise in the future as life expectancy and the median age of the population continue to increase.

Inflammatory diseases are known which affect many diverse tissues and organs in the body. Examples of diseases in which the inflammation is most apparent in the joints and related connective tissue are osteoarthritis, rheumatoid arthritis, tendonitis, bursitis, and the like. These diseases are most often treated with nonsteroidal antiinflammatory agents such as aspirin, ibuprofen, and piroxicam, or with antiinflammatory glucocorticosteroids. However, these treatments suffer either from a lack of efficacy in completely controlling the disease process, or from unacceptable toxic side effects.

Arthritis is a progressive disorder of unknown cause that principally affects the hands and large weight-bearing Joints and is clinically characterized by pain, deformity, and limitation of motion. Pathologically, it is characterized by erosive lesions, cartilage destruction, subchondral sclerosis, cyst formation, and osteophytes at the joint margins.

Arthritis is a potentially crippling disease that is second only to cardiovascular diseases in producing severe chronic disability (Epstein, *New England J. Med.*, 20 239, 1322 (1989)). It affects nearly 10 percent of the population over age 60. This high incidence rate results in billions of dollars in costs annually for medications, surgery, and lost productivity (Peyron, *Clin. Orthop.*, 213, 13 (1986); Holbrook, *Am. Acad. Orthopaedic Surgeons,* 1 (1984)). Thus treatment to arrest and/or reverse the progress of arthritis would be of considerable benefit to mankind.

BACKGROUND OF THE INVENTION

J. Faust, *Z. Chem.* 8, 170–1 (1968), describes the preparation of:

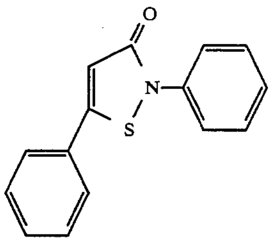

and claims no potential use for this compound. S. N. Lewis, et. al., in U.S. Pat. No. 4,105,431, describe syntheses of:

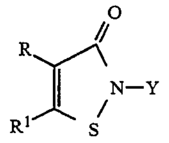

wherein Y is an unsubstituted or substituted alkyl, alkenyl, or alkynyl group of 1 to 18 carbon atoms, preferably 4 to 18 carbon atoms, an unsubstituted or substituted cycloalkyl group having a 3 to 12 carbon atom ring, an unsubstituted or substituted aralkyl group of up to 10 carbon atoms, or an unsubstituted or substituted aryl group of up to 10 carbon atoms; R is hydrogen, halogen, or a ($C_1$–$C_4$) alkyl group, and $R^1$ is hydrogen, halogen, or a ($C_1$–$C_4$) alkyl group, provided that when Y is methyl or ethyl then both R and $R^1$ may not be hydrogen. These compounds have been claimed as biocides in the control of microorganisms.

M.D. Scott, et. al., *J. Chem. Soc., Perkin Trans. I* 1 (12), 1432–4 (1972), describe the preparation of:

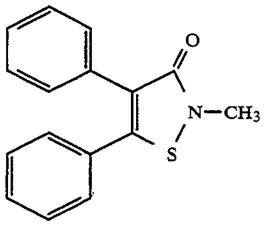

and claim no potential use for this compound.

G. Le Coustumer and Y. Mollier, *Bull. Soc. Chim. Fr.* 8–9, 3076–87 (1970), describe the synthesis of:

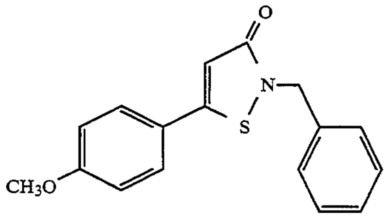

and claim no potential use for this compound.

J. Faust, *Z. Chem.* 15 (12), 478–9 (1975), describes the preparation of:

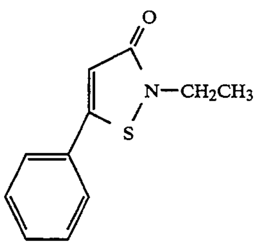

and claims no potential use for this compound.

J. Goerdeler and M. Roegler, *Chem. Ber.* 103 (1), 12–1 (1970), describe the synthesis of:

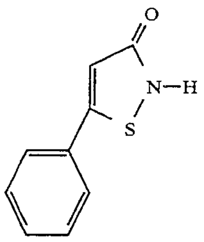

and claim no potential use for this compound.

K. Furuya, in Japanese Patent 63,201,654, describes compounds of the general structure:

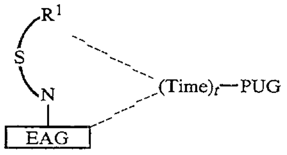

in which $R^1$ indicates a group of atoms which is required in order to form a 3-to 8-member simple or condensed hetero-ring by bonding with the nitrogen atom (N) and sulfur atom (S). EAG indicates a group which accepts electrons from reducing substances. N and S indicate a nitrogen atom and a sulfur atom, respectively. Time indicates a group which releases the PUG via a reaction which is triggered by the cleavage of the nitrogen-sulfur single bond in the formula. PUG indicates a photographically useful group, and t indicates 0 or 1. The solid lines in the formula indicate actual bonds, while the broken lines indicate alternative bonds (i.e. at least one of the broken lines indicates a bond). Compounds of this general structure have been claimed as silver halide photosensitive materials.

Within this disclosure are described the compounds shown below:

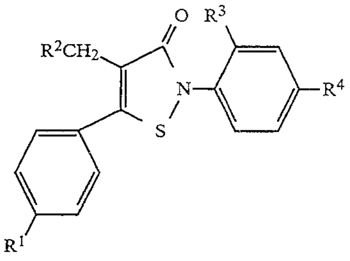

| $R^1$ | $R^2$ | $R^3$ | $R^4$ |
|---|---|---|---|
| H | 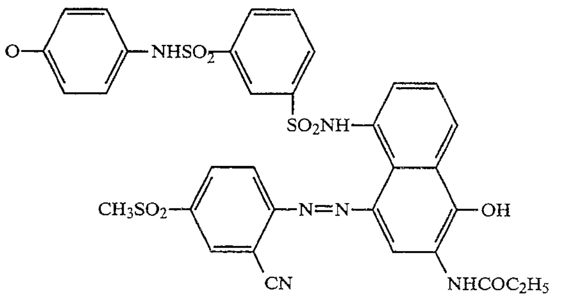 | $NO_2$ | $SO_2N(C_{18}H_{37})CH_3$ |
| $OC_{16}H_{33}$ | 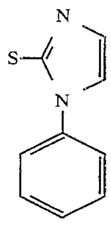 | $SO_2N(C_2H_5)_2$ | $NO_2$ |

-continued

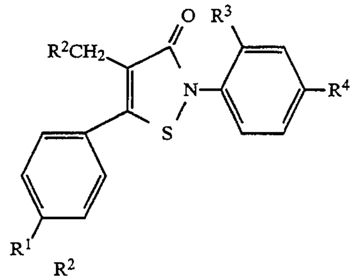

| $R^1$ | $R^2$ | $R^3$ | $R^4$ |
|---|---|---|---|
| H | 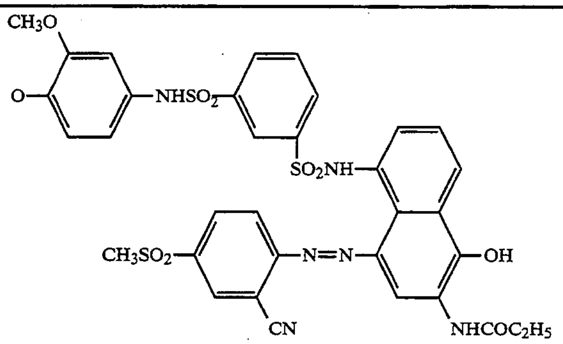 | $NO_2$ | $CONHC_{16}H_{33}$ |

None of the above-described references disclose, or would lead one to, compounds of the present invention.

SUMMARY OF THE INVENTION

The present invention describes compounds of Formula (I), processes for their preparation, pharmaceutical compositions containing them and therapeutic methods for their use in treating thrombosis and in particular, describes a method of treating inflammatory conditions in a mammal by administering a compound of the Formula (I) wherein

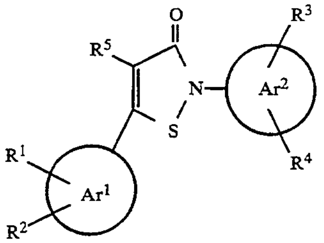

(I)

$Ar^1$ and $Ar^2$ are each independently a $C_5$ to $C_{10}$ saturated or unsaturated carbocyclic ring or a $C_5$ to $C_{10}$ heterocyclic ring containing at least one nitrogen, sulfur or oxygen and selected from the group consisting essentially of: phenyl, phenethyl, phenoxy, naphthyl, napthyridinyl, thiazolyl, thiophenyl, thienyl, furyl, pyrrolyl, pyridyl, indolyl, quinolyl, imidazolyl, isoquinolyl, benzyl, benzyloxy, benzofuryl, benzothienyl, benzothiazolyl, pyrimidyl, pyrazinyl, quinazolyl, and phthalazinyl;

$R^1$ $R^2$ $R^3$ and $R^4$ each are independently: H, straight or branched alkyl chain of 1 to 6 carbon atoms, substituted with 0–3 $R^8$, alkenyl of 2–4 carbon atoms, alkynyl of 2 to 4 carbon atoms, F, Cl, Br, I, OH, $OR^6$, $CO_2H$, $OCOR^6$, $OCO_2R^6$, $OCON(R^6)_2$, $CF_3$, $NO_2$, $NR^6R^7$, $NHR^7$, $NR^6C(=O)$ $R^6$, $NR^6C$ $(=0)$ $OR^6$, $NC(S)_2R^6$, $NR^6C(=0)N(R^6)_2$, $NR^6SOR^6$, $N(SO_2R^6)_2$,$N(SO_2CF_3)_2$, $SR^6S(O)R$-$^6SO_2R^7$, $SO_3H$, $SO_2N(R^6)_2$, $SO_2NR^6R^7$, $COR^6$, $CO_2R^6$, $CON(R^6)_2$, $C(S)_2NHR^6$, $C(S)_2N(R^6)_2$, $CONR^6OR^6$, CN, $CONH_2$, $CONHR^6$, $R^6CO_2R^7$, tetrazolyl, or hydroxamic acid;

$R^5$ is H, Br, $OR^6$, $SR^6$, $COR^6$, $CO(R^1$-$R^4$ substituted $Ar^1)$, $R^6$, $CO_2R^6$, $CO_2H$, $CONH_2$, $CONHR^6$, $CON(R^6)_2$, $CONH(R^1$-$R^4$ substituted $Ar^1)$, CON $(R^1$-$R^4$ substituted $Ar^1)_2$, CN or $R^1$-$R^4$ substituted $Ar^1$;

$R^6$ is straight or branched alkyl chain of 1 to 4 carbon atoms, alkenyl of 3–4 carbon atoms, or alkynyl of 3–4 carbon atoms;

$R^7$ is H, straight or branched alkyl chain of 1to 4 carbon atoms, alkenyl of 2–4 carbon atoms, or $COR^6$; and $R^8$ is: H, straight or branched alkyl chain of 1 to 6 carbons substituted with 0–3 $R^6$ alkenyl of 2–4 carbon atoms, alkynyl of 2–4 carbon atoms, OH, $OR^6$, $CO_2H$, $OCOR^6$, $OCO_2R^6$, $OCON(R^6)_2$, $NO_2$, $NR^6R^7$, $NHR^7$, $NR^6C(=O)R^6$, $NR^6C(=O)OR^6$, $N(C(=S)R^6)_2$, $NR^6C(=O)N(R^6)_2$, $NR^6SO_2R^6$, N $(SO_2R^6)_2$, $SR^6$, $S(0)R^6$, $SO_2R^7$, $SO_3H$, $SO_2N(R^6)_2$, $SO_2NR^6R^7$, $COR^6$, $CO_2R^6$, $CON(R^6)_2$, $C(=S)$ $NHR^6$, $C(=S)N(R^6)_2$, $CONR^6OR^6$, CN, $CONH_2$, $CONHR^6$, $R^6CO_2$, tetrazolyl, and hydroxamic acid; with the proviso that $R^1$-$R^5$ may not simultaneously be H when $Ar^1$ and $Ar^2$ are each phenyl.

Within the compounds of the invention described herein are the pharmaceutically acceptable salts of such compounds including acid addition salts and base addition salts. The term "pharmaceutically acceptable salts" embraces salts commonly used to form alkali metal salts and to form addition salts of free acids or free bases. The nature of the salt is not critical, provided that it is pharmaceutically acceptable. Suitable, pharmaceutically acceptable acid addition salts of compounds of the invention may be prepared from an inorganic acid or from an organic acid. Suitable, pharmaceutically acceptable base addition salts of the compounds include metallic salts made of aluminum, calcium, lithium, magnesium, potassium, sodium, or zinc or organic salts. All of these salts may be prepared by conventional means from the corresponding conjugates described herein by reacting, for example, the appropriate acid or base with the compound.

General Synthesis

The compounds of Formula (I) may be prepared by the reactions outlined herein. All transformations are carried out using solvents compatible with reagents. When appropriate, protecting groups may be employed in order to carry out a transformation and this should be readily apparent to one skilled in the art.

The compounds of Formula (I), in which $R^5$ is hydrogen, may be prepared conveniently through the series of reactions outlined in Scheme 1. Thus, treatment of an appropriately substituted Scheme 1

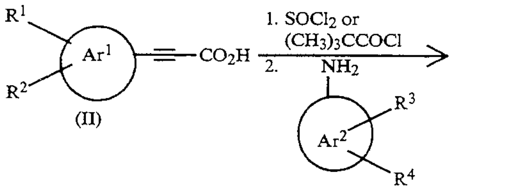

(II) (III)

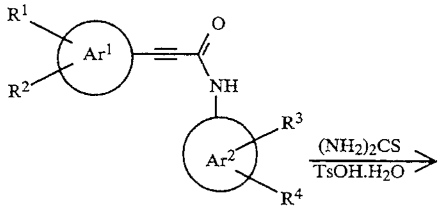

(IV)

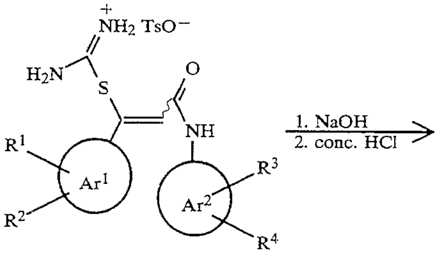

(V)

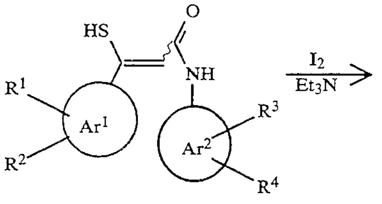

(VI)

-continued

Scheme 1

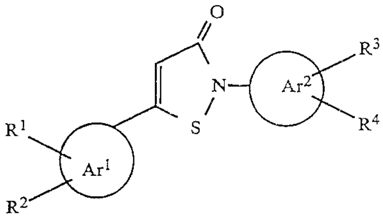

(VII)

phenylpropiolic acid (II) (for general synthetic procedures for production of substituted phenylpropiolic acids see: S. Chimichi, et. al., *J. Heterocyclic Chem.* 20, 105 (1983) and M. Reimer, et. al., *J. Am. Chem. Soc.*, 64, 2510 (1942)) with either thionyl chloride (A. Yokoyama, K. Ashida and H. Tanaka, *Chem. Pharm. Bull.* 12 (6), 690–695 (1964)) or trimethylacetyl chloride in an inert solvent such as benzene, followed by addition of an appropriately substituted arylamine (III), many of which are commercially available, leads to formation of compounds of Formula (IV). Treatment of compounds of Formula (IV) with thiourea and p-toluenesulfonic acid monohydrate (A. Yokoyama, K. Ashida and H. Tanaka, *Chem. Pharm. Bull.* 12 (6), 690–695 (1964)) in absolute ethanol leads to formation of compounds of Formula (V) . Hydrolysis of compounds of Formula (V) with base, for example sodium hydroxide (A. Yokoyama, K. Ashida and H. Tanaka, *Chem. Pharm. Bull.* 12 (6), 690–695 (1964)), in 50% aqueous ethanol, followed by acidification, results in formation of compounds of Formula (VI). Treatment of compounds of Formula (VI) with iodine and triethylamine (*J. Faust Z. Chem.* 8, 170–171 (1968)) in methylene chloride provides compounds of Formula (VII).

The compounds of Formula (I), in which $R^5$ is not bromine, may be prepared through the sequence of reactions described in Scheme 2. Thus treatment of an appropriately substituted arylamide (VIII) with a base, for example lithium diisopropylamide (LDA), followed by addition of an appropriately substituted Scheme 2

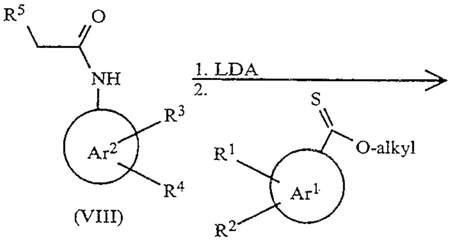

(VIII) (IX)

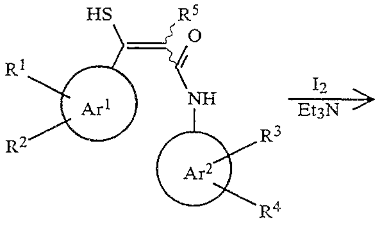

(X)

-continued

Scheme 2

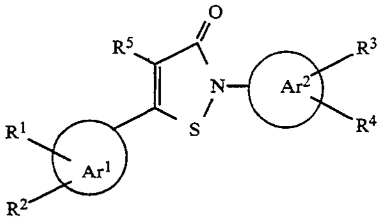

(XI)

O-alkylthio compound (IX), for example O-ethylthiobenzoate (S. O. Lawesson, et. al., *Bull Soc. Chim. Belg.* 87 (4) 293 (1978)), leads to formation of compounds of Formula (X). Treatment of (X) with iodine and triethylamine, similar to the conversion of (VI) to (VII) in Scheme 1, leads to formation of compounds of Formula (XI).

The compounds of Formula (I), in which $R^5$ is bromine, may be prepared according to Scheme 3. Thus treatment of compounds of Formula (VII) with bromine and triethylamine in ethyl acetate, similar to that described by Sheldon N. Lewis, George A. Miller, Martin Hausman and Eugene C. Szamborski, *J. Heterocyclic Chem.* 8, 571–580 (1971), provides compounds of Formula (XII).

Scheme 3

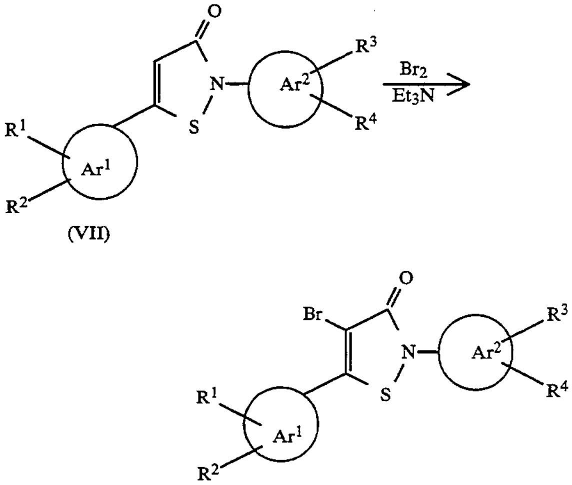

(VII)

(XII)

EXPERIMENTAL

The preparations of various substituted 2,5-diaryl-4-isothiazolin-3-ones are described below. All transformations were carried out under an atmosphere of dry nitrogen. Evaporation of solvent was carried out on a rotary evaporator at reduced pressure using a water aspirator. Solutions were dried over anhydrous magnesium sulfate. Tetrahydrofuran was dried over sodium metal and N,N-dimethylformamide was dried over molecular sieves. NMR refers to proton nuclear magnetic resonance spectra which were run at either 200 or 300 mHz; abbreviations for NMR data are the following: s=singlet, bs=broad singlet, d=doublet, t=triplet, q=quartet, m=multiplet, $CDCl_3$=25 deuterochloroform, $d_6$-DMSO=hexadeuterodimethyl sulfoxide. All NMR spectra were recorded as parts per million downfield from the internal standard tetramethylsilane (TMS). IR refers to infrared spectra which were recorded in reciprocal centimeters ($cm^{-1}$).

EXAMPLE 1

Compound of Formula (I) in which $R^1$, $R^2$, $R^4$ and $R^5$=H, $Ar^1$=$Ar^2$=phenyl and $R^3$=4-$CH_3$ Part A: N- (4-Methylphenyl) phenylpropiolamide A mixture of 14.61 g (0.10 mole) phenylpropiolic acid, 14.28 g (0.12 mole) thionyl chloride and 50 mL benzene was stirred and heated between 60°–70° C. for 3 hrs. The reaction was allowed to cool to room temperature and solvent was evaporated. The reaction vessel was charged with 50 mL of fresh benzene and the mixture cooled in an ice bath. Added next, dropwise in 50 mL benzene, was 21.43 g (0.20 mole) of 4-toluidine. After addition was complete, the ice bath was removed and the mixture stirred at room temperature for one hour. The mixture was poured into 200 mL cold water and the layers were separated. The aqueous layer was extracted with three 100 mL portions of ethyl acetate. The combined organic layers were then washed sequentially with 100 mL portions of 5% aqueous hydrochloric acid, water, 5% aqueous sodium carbonate and water. The organic layer was dried, filtered and solvent was evaporated from the filtrate. The resulting solid was recrystallized twice from ethanol/water to provide 11.58 g (49.20 mmol, 49%) N-(4-methylphenyl) phenylpropiolamide as a white powder, mp=139°–141°. NMR ($CDCl_3$/TMS): 2.35 (S, 3H), 7.1–7.6 (m, 10H). IR (Nujol):2214, 1636. High resolution mass spectrum: Calculated; 236. 107539. Measured; 236. 107101. Anal. calcd. for $C_{16}H_{13}NO$: C 81.70, H 5.53, N 5.96; Found C 3581.55, H 5.40, N 6.05.

Part B: S-(1-Phenyl-2-((4 -methylphenyl) carbamoyl)vinyl) isothiuronium-p-toluenesulfonate A mixture of 4.70 g (0.02 mole) N-(4-methylphenyl) phenylpropiolamide, 1.52 g (0.02 mole) thiourea, 3.80 g (0.02 mole) p-toluenesulfonic acid monohydrate and 40 mL absolute ethanol was stirred at reflux for 3 hrs. The reaction was allowed to cool to room temperature and 100 mL diethyl ether was added. The resulting solid was suction filtered to provide 8.26 g (17.00 mmol, 85%) S-(1-Phenyl-2-((4-methylphenyl)carbamoyl)vinyl) isothiuronium-p-toluenesulfonate as a white powder, mp=204°–205.5° C. NMR ($d_6$-DMSO/TMS): 2.25 (S, 3H), 2.3 (S, 3H), 7.05–7.6 (m, 13H), 9.2 (bs, 4H), 10.1 (S, 1H). IR (Nujol): 1688 . Anal. calcd. for $C_{24}H_{25}N_3O_4S_2$: C 59.63, H 5.18, N 8.70, S 13.25; Found C 59.36, H 5.24, N 8.60, S 13.31.

Part C: N-(4-Methylphenyl)-3-mercapto-3-phenylpropenamide

A mixture of 8.02 g (16.60 mmol) S-(1-Phenyl-2-((4-methylphenyl)carbamoyl)vinyl)isothiuronium-p-toluenesulfonate, 2.66 g (33.20 mmol) of 50% aqueous sodium hydroxide and 200 mL of 50% aqueous ethanol was stirred at reflux for 2 hrs. The mixture was allowed to cool to room temperature and added was 200 mL water. The mixture was washed with three 100 mL portions of diethyl ether and the aqueous layer was cooled in an ice bath. The solution was acidified to pH 3 with concentrated hydrochloric acid. The resulting solid was suction filtered, thoroughly washed with water and air dried overnight. Obtained was 2.68 g (9.90 mmol, 59%) N-(4-methylphenyl)-3-mercapto-3-phenylpropenamide as a pale, yellow powder, mp=113°–114° C.- NMR ($CDCl_3$/TMS): 2.35 (S, 3H), 6.15 (S, 1H), 7.1 (bs, 1H), 7.15–7.6 (m, 9H), 8.45 (bs, 1H). IR (Nujol):

1626. High resolution mass spectrum: Calculated; 270.095261. Measured; 270.094538. Anal. calcd. for $C_{16}H_{15}NOS$: C 71.38, H 5.58, N 5.20, S 11.90; Found C 71.29, H 5.53, N 5.29, S 11.80.

Part D: N-(4-methylphenyl)-5-phenyl-4-isothiazolin-3-one

A mixture of 1.34 g (5.00 mmol) N-(4-methylphenyl)-3-mercapto-3-phenylpropenamide and 100 mL methylene chloride was stirred at room temperature. Added, portionwise, was 1.27 g (5.00 mmol) iodine followed by 1 mL (excess) triethylamine and the mixture stirred for one hour. Solvent was evaporated and the residue triturated under ethyl acetate. The solid was filtered and solvent evaporated from the filtrate. The resulting residue was purified by flash chromatography using hexanes-ethyl acetate (3:2) as eluant. Obtained was 0.70 g (2.60 mmol, 52%) N-(4-methylphenyl)-5-phenyl-4-isothiazolin-3-one as a very pale, yellow powder, mp=110°-112° C. NMR ($CDCl_3$/TMS): 2.4 (S, 3H), 6.6 (S, 1H), 7.25-7.6 (m, 9H). IR (Nujol): 1650. High resolution mass spectrum: Calculated; 268.079611. Measured; 268.078308. Anal. calcd. for $C_{16}H_{13}NOS$: C 71.91, H 4.49, N 5.24, S 11.98; Found C 71.85, H 4.69, N 5.21, S 11.86.

Similarly prepared by the method used to synthesize Example 1 were Examples 11-34.

EXAMPLE 2

Compound of Formula (I) in which $R^1$, $R^2$, $R^3$ and $R^4$=H, $Ar^1$=$Ar^2$=phenyl and $R^5$=Br A mixture of 0. 759 g (0. 003 mole) N, 5-diphenyl-4-isothiazolin-3-one (J. Faust, *Z. Chem.* 8; 170-1 (1968)), 0.300 g (0.003 mole) triethylamine and 10 mL ethyl acetate was stirred at −5° C. Added, dropwise, was 0.480 g (0.003 mole) bromine dissolved in 5 mL ethyl acetate. The mixture was stirred at −50° C. for 30 min. followed by stirring at room temperature for 3 hrs. Solvent was evaporated and the residue purified by flash chromatography using a mixture of hexanes-ethyl acetate (2:1) as eluant. Obtained was 0.190 g (5.720 mmol, 19%) 4-bromo-N,5-diphenyl-4-isothiazolin-3-one as a very pale, yellow powder, mp=114°-117° C. NMR ($CDCl_3$/TMS): 7.3-7.8 (m, 10H). IR (Nujol): 1662. High resolution mass spectrum: Calculated (for $^{81}Br$ isotope); 333. 972426. Measured; 333.972673. Anal. calcd. for $C_{15}H_{10}NOSBr$: C 54.22, H 3.01, N 4.22, S 9.64, Br 24.10; Found: C 54.11, H 3.16, N 4.30, S 9.58, Br 23.91.

Example 3

Compound of Formula (I) in which $R^1$, $R^2$, $R^4$ and $R^5$=H, $Ar^1$=$Ar^2$=phenyl and $R^3$=4-$CO_2H$ A mixture of 1.449 g (0.005 mole) N-(4-carboxyphenyl)-3-mercapto-3-phenylpropenamide (A. Yokoyama, K. Ashida and H. Tanaka, *Chem. Pharm. Bull.* 12 (6), 690-5 (1964)), 3 mL (excess) triethylamine, 100 mL water and 100 mL ethanol was stirred at room temperature. Added, portionwise, was 1.269 g (0.005 mole) iodine and the mixture stirred at room temperature for 3 hrs. The solution was filtered and the filtrate was acidified to pH 1 with concentrated hydrochloric acid. The resulting solid was filtered and recrystallized twice from ethanol/water to provide 0.350 g (1.180 mmol, 23%) N-(4-carboxyphenyl)-5-phenyl-4-isothiazolin-3-one as a white powder, mp=238°-240° C. NMR ($CDCl_3$/TMS): 6.6 (S, 1H), 7.5-7.6 (m, 5H), 7.9 (d, 2H), 8.2 (d, 2H). IR (Nujol): 3481, 1698, 1619. High resolution mass spectrum: Calculated; 298.053790. Measured; 298.053472. Anal. calcd. for $C_{16}H_{11}NO_3S$: C 64.65, H 3.70, N 4.71, S 10.77; Found C 64.52, H 3.64, N 4.59, S 10.75.

Similarly prepared by the method used to synthesize Example 3 were Examples 35 and 36.

EXAMPLE 4

Compound of Formula (I) in which $R^1$, $R^2$, $R^4$ and $R^5$=H, $Ar^1$ =$Ar^2$=phenyl and $R^3$=4-$CO_2Et$ A mixture of 0.120 g (0.404 mmol) N-(4-carboxyphenyl)-5-phenyl-4-isothiazolin-3-one, 1.000 g (excess) anhydrous sodium bicarbonate, 2 mL (excess) iodoethane and 25 mL N,N-dimethylformamide was stirred at 70° C. for 3 hrs. The mixture was poured into water and extracted with three 50 mL portions of ethyl acetate. The organic layers were combined, dried, filtered and solvent was removed. The residue was purified by flash chromatography on silica gel using a mixture of hexanes-ethyl acetate (2:1) as eluant. Obtained was 0.090 g (0.277 mmol, 68%) N-(4-carbethoxyphenyl)-5-phenyl-4-isothiazolin-3-one as a pale, yellow powder, mp=134°-135° C. NMR ($CDCl_3$/TMS): 1.4 (t, 3H), 4.4 (q, 2H), 6.6 (s, 1H), 7.55 (m, 4H), 7.8 (d, 2H), 8.15 (d, 2H). IR (Nujol): 1703, 1664. High resolution mass spectrum: Calculated; 325.077265. Measured; 325.077132. Anal. calcd. for $C_{18}H_{15}NO_3S$: C 66.46, H 4.62, N 4.31, S 9.85; Found C 66.35, H 4.71, N 4.22, S 9.90.

Similarly prepared by the method used to synthesize Example 4 were Examples 37 and 38.

EXAMPLE 5

Compound of Formula (I) in which $R^1$, $R^2$, $R^4$, and $R^5$=H, $Ar^1$=$Ar^2$=phenyl and $R^3$=4-$CONH_2$ A mixture of 1.000 g (3.367 mmol) N-(carboxyphenyl)-5-phenyl-4-isothiazolin-3-one, 1 mL (excess) thionyl chloride and 20 mL benzene was stirred at 60°-70° C. for 3 hrs. The reaction was allowed to cool to room temperature and solvent was evaporated. The reaction vessel was charged with 20 mL of fresh benzene and the mixture cooled in an ice bath. Added, dropwise with stirring, was 5 mL (excess) of 30% ammonium chloride solution and the mixture stirred 30 mins. The resulting solid was filtered and recrystallized from absolute ethanol to provide 0.670 g (2.260 mmol, 67%) N-(4-carboxamidophenyl)-5-phenyl-4-isothiazolin-3-one as a pale, yellow powder, mp=219°-220° C. NMR ($d_6$-DMSO/TMS): 7.0 (S, 1H), 7.4-8.1 (m, 11H). IR (Nujol): 3392, 3210, 1646, 1606. High resolution mass spectrum: Calculated; 297.069775. Measured; 297.069698. Anal. calcd. for $C_{16}H_{12}N_2O_2S$: C 64.85, H 4.08, N 9.45, S 10.82; Found C 64.58, H 4.03, N 9.39, S 10.76.

EXAMPLE 6

Compound of Formula (I) in which $R^1$, $R^2$, $R^4$ and $R^5$=H, $Ar^1$=$Ar^2$=phenyl and $R^3$=2-$NH_2$ A mixture of 0.560 g (1.880 mmol) N-(2-nitrophenyl)-5-phenyl-4-isothiazolin-3-one, 0.450 g (excess) iron powder, 1 mL glacial acetic acid and 15 mL absolute ethanol was stirred at reflux for one hour. The mixture was allowed to cool to room temperature, poured into 150 mL water and extracted with three 100 mL portions of ethyl acetate. The organic layers were combined, dried, filtered and solvent was evaporated. The resulting solid was recrystallized from ethanol/water to provide 0.250 g (0.930 mmol, 49%) N-(2-aminophenyl) -5-phenyl-4-isothiazolin-3-one, mp=145°-146° C.- NMR ($CDCl_{13}$/TMS): 4.15 (bs, 2H), 6.6 (s, 1H), 6.8-7.6

(m, 9H). IR (Nujol): 3358, 3216, 1658. High resolution mass spectrum: Calculated; 269. 074860. Measured; 269.074265. Anal. calcd. for $C_{15}H_{12}N_2OS$: C 67.14, H 4.51, N 10.44, S 11.95; Found C 66.76, H 4.43, N 10.19, S 12.09.

Similarly prepared by the method used to synthesize Example 6 were Examples 39 and 40.

EXAMPLE 7

Compound of Formula (I) in which $R^1$, $R^2$, $R^4$ and $R^5$=H, $Ar^1$=$Ar^2$=phenyl and $R^3$=4-N($SO_2CF_3$)$_2$ A mixture of 0.200 g (0.745 mole) N-(4-aminophenyl)-5-phenyl-4-isothiazolin-3-one, 0.3 mL (excess) triethylamine, 0.003 g (catalytic) 4-dimethylaminopyridine and 10 mL methylene chloride was stirred at room temperature. Added was 0.200 g (excess) trifluoromethanesulfonyl chloride in 1 mL methylene chloride and the mixture stirred 2 hrs. Solvent was evaporated and the residue was purified by flash chromatography on silica gel using a mixture of hexanesethyl acetate (2:3) as eluant. Obtained was 0.230 g (0.432 mole, 58%) N-(4-(bistrifluoromethane)sulfonamidophenyl)-5-phenyl-4-isothiazolin-3-one as a white powder, mp=184°-186.5° C. NMR ($CDCl_3$/TMS): 6.60 (s, 1H), 7.45-7.60 (m, 7H), 7.95 (d, 2H). IR (Nujol): 1662. High resolution mass spectrum: Calculated; 532.973432. Measured; 532.973073.

EXAMPLE 8

Compound of Formula (I) in which $R^1$, $R^2$, $R_3$, $R_4$ and $R^5$=H, $Ar^1$=phenyl and $Ar^2$=2-benzothiazolyl Part A: N-(2-benzothiazolyl)phenylpropiolamide A mixture of 14.61 g (0.10 mole) phenylpropiolic acid, 14.28 g (0.12 mole) thionyl chloride and 50 mL benzene was heated between 60°-70° C. for 3 hrs. The reaction was allowed to cool to room temperature and solvent was evaporated. The reaction vessel was charged with 50 mL of fresh benzene and the mixture cooled in an ice bath. Added next, dropwise in 50 mL dry tetrahydrofuran, was 30.40 g (0.20 mole)2-aminobenzothiazole. After addition was complete the ice bath was removed and the mixture stirred at room temperature for one hour. The mixture was poured into 200 mL cold water and the layers were separated. The aqueous layer was extracted with three 100 mL portions of ethyl acetate. The combined organic layers were then washed sequentially with 100 mL portions of 5% aqueous hydrochloric acid, water, 5% aqueous sodium carbonate and water. The organic layer was dried, filtered and solvent was evaporated from the filtrate. The residue was semi-purified by flash chromatography on silica gel using a mixture of hexanes-ethyl acetate (3:1) as eluant. Solvent was evaporated from the two-component mixture that was obtained. The resulting solid was recrystallized from absolute ethanol to provide 1.02 g (3.66 mmol, 3.6%)1-oxo-7-phenyl-1H-pyrimido[6,1-b]benzothiazole as a pale, yellow powder, mp=196°-197° C. NMR ($CDCl_3$/TMS): 6.85-8.5 ( m, 9H), 9.15 (m, 1H). IR (Nujol): 1674. High resolution mass spectrum: Calculated; 279.059210. Measured; 279.058859. Anal. calcd. for $C_{16}H_{10}N_2OS$: C 69.05, H 3.62, N 10.06, S 11.52; Found C 69.03, H 3.54, N 9.99, S 11.52.

Solvent was removed from the mother liquor and the resulting solid was recrystallized three times from methylene chloride to provide 1.12 g (4.02 mmol, 4%) N-(2-benzothiazolyl)phenylpropiolamide as a white powder, mp=174°-176° C. NMR ($CDCl_{13}$/TMS): 7.2-8.0 (m, 9H), 12.65 (bs, 1H). IR (Nujol): 3162, 2206, 1648. High resolution mass spectrum: Calculated; 279.059210. Measured; 279.058656. Anal. calcd. for $C_{16}H_{10}N_2OS$: C 69.05, H 3.62, N 10.06, S 11.52; Found C 68.66, H 3.52, N 9.98, S 11.38.

Part B: S-(1-Phenyl-2-((2-benzothiazolyl)carbamoyl)-vinyl)isothiuronium-p-toluenesulfonate A mixture of 1. 010 g (3.630 mmol) N-(2-benzothiazolyl) phenylpropiolamide, 0.276 g (3.630 mmol) thiourea, 0.690 g (3.630 mmol) p-toluenesulfonic acid monohydrate and 10 mL absolute ethanol was stirred at reflux for 3 hrs. The mixture was allowed to cool to room temperature and 100 mL diethyl ether was added. The resulting solid was filtered and dissolved in 20 mL hot ethanol. The mixture was allowed to cool to room temperature and 100 mL diethyl ether was added. The resulting solid was filtered and suction dried to provide 0.810 g (1.530 mmol, 42%) S-(1-phenyl-2-((2-benzothiazolyl)carbamoyl)vinyl) isothiuronium-p-toluenesulfonate as a yellow powder, mp=142°-146° C. NMR ($d_6$-DMSO/TMS): 2.3 (s, 3H), 7.0 (s, 1H), 7.05-7.95 (m, 13H), 9.2 (bs, 2H), 9.4 (bs, 2H), 12.65 (bs, 1H). IR (Nujol): 1664.

Part C: N-(2-benzothiazolyl)-3-mercapto-3-phenylpropenamide

A mixture of 0.67 g (1.27 mmol) S-(1-phenyl-2-((2-benzothiazolyl)carbamoyl)vinyl)isothiuronium-p-toluenesulfonate, 0.21 g (2.60 mmol) of 50% aqueous sodium hydroxide and 10 mL of 50% aqueous ethanol was stirred at reflux for 2 hrs. The mixture was allowed to cool to room temperature and added was 100 mL water. The mixture was washed with three 100 mL portions of diethylether and the aqueous layer was cooled in an ice bath. The solution was acidified to pH 3 with concentrated hydrochloric acid. The resulting solid was suction dried to provide 0.27 g (0.86 mmol, 68%) N-(2-benzothiazolyl)-3-mercapto-3-phenylpropenamide as a pale, yellow powder, mp=168°-172° C. NMR ($CDCl_3$/TMS): 6.25 (s, 1H), 7.25-7.9 (m, 11H). IR (Nujol): 3500, 3128, 1648. Anal. calcd. for $C_{16}H_{12}N_2OS_2$: C 61.51, H 3.87, N 8.97, S 20.53; Found C 61.54, H 3.72, N 9.07, S 20.56.

Part D: N-(2-benzothiazolyl)-5-phenyl-4-isothiazolin-3-one

A mixture of 0.250 g (0.800 mmol) N-(2-benzothiazolyl)-3-mercapto-3-phenylpropenamide and 10 mL methylene chloride was stirred at room temperature. Added was 0.203 g (0.800 mmol) iodine dissolved in 10 mL methylene chloride and the mixture stirred 5 mins. Added next was 0.5 mL (excess) triethylamine and the mixture stirred for one hour. Solvent was evaporated and the residue dissolved in ethyl acetate and washed with water. The organic layer was dried, filtered and solvent was evaporated. The resulting solid was recrystallized from absolute ethanol to provide 0.090 g (0.290 mmol, 36%) N-(2-benzothiazolyl)-5-phenyl-4-isothiazolin-3-one as a very pale, yellow solid, mp=201°-202° C. NMR ($CDCl_3$/TMS): 6.6 (s, 1H)7.3-7.95 (m, 9H). IR (Nujol): 1680. High resolution mass spectrum: Calculated; 311.031282. Measured; 311.030775. Anal. calcd. for $C_{16}H_{10}N_2OS_2$: C 61.91, H 3.25, N 9.03, S 20.66; Found C 61.82, H 3.14, N 8.97, S 20.55.

Similarly prepared by the method used to synthesize Example 8 was Example 41.

EXAMPLE 9

Compound of Formula (I) in which $R^2$, $R^3$, $R_4$ and $R^5$=H, $Ar^1$=$Ar^2$=phenyl and $R^1$=4-$CO_2H$ Part A: 3-(4-bromophenyl)-N-phenylpropiolamide A mixture of 8.50 g (37.77 mmol) (4-bromophenyl) propiolic acid (S. Chimichi, et. al., *J. Heterocyclic Chem.* 20, 105 (1983)), 5.39 g (45.32 mmol, 1.2 equivs.) thionyl chloride and 50 mL benzene was stirred and heated at 75° C. for 3 hrs. The reaction was allowed to cool to room temperature and solvent was evaporated. The reaction vessel was charged with 50 mL of fresh benzene and the mixture cooled in an ice bath under an atmosphere of nitrogen. Added next, dropwise in 50 mL benzene, was 7.04 g (75.54 mmol, 2 equivs.) aniline. After addition was complete, the ice bath was removed and the mixture stirred at room temperature overnight. The mixture was poured into 150 mL water and the layers were separated. The aqueous layer was extracted with three 100 mL portions of ethyl acetate. The combined organic layers were then washed sequentially with 100 mL portions of 5% aqueous hydrochloric acid, water, 5% aqueous sodium carbonate and water. The organic layer was dried, filtered and solvent was evaporated from the filtrate. The resulting solid was recrystallized from absolute ethanol to provide 3.93 g (13.09 mmol, 35%)3-(4-bromophenyl)-N-phenylpropiolamide as a white powder, mp=159°-160.5° C. NMR ($CDCl_3$/TMS): 7.15 (t, 1H), 7.32-7.40 (m, 4H), 7.49 (d, 2H), 7.57 (d, 2H), 7.80 (bs, 1H). IR (KBr): 3304, 2214, 1638. High resolution mass spectrum: Calculated; 298.994575 (for $^{79}Br$ isotope). Measured; 298. 994225.

Part B: 3-(4-Carboxyphenyl)-N-phenylpropiolamide

A mixture of 1.66 g (41.65 mmol, 5 equivs.) sodium hydride and 30 mL dry tetrahydrofuran was stirred at room temperature. Added dropwise, in 30 mL dry tetrahydrofuran, was 2.50 g (8.33 mmol) 3-(4-bromophenyl)-N-phenylpropiolamide and the mixture stirred for 4 hrs. The mixture was then cooled to −78° C. and added dropwise was 6.33 mL (1.9 equivs.) of 2.5M n-butyllithium (in hexanes). After addition was complete, the solution was stirred at −78° C. for 30 mins. Carbon dioxide was bubbled through the solution as the cooling bath was removed. Carbon dioxide was bubbled through an additional one hour at room temperature. The mixture was carefully quenched with 5 mL methanol and the solution poured into 100 mL water. The layers were separated and the aqueous layer was washed with three 100 mL portions of diethyl ether. The aqueous layer was acidified with concentrated hydrochloric acid. The yellow precipitate which resulted was filtered and recrystallized from absolute ethanol to provide 1.01 g (3.80 mmol, 46%) 3-(4-carboxyphenyl)-N-phenylpropiolamide as a pale, yellow powder, mp=271°-272° C. 30 NMR ($d_6$-DMSO/TMS): 7.12 (t, 1H), 7.35 (t, 2H), 7.64 (d, 2H), 7.77 (d, 2H), 8.02 (d, 2H), 10.96 (bs, 1H)13.31 (bs, 1H). IR (KBr): 3310, 2214, 1702, 1642. Mass spectrum (CI): M/z=266 $(M+H)^+$. Anal. calcd. for $C_{16}H_{11}NO_3$: C 72.45, H 4.18, N 5.28; Found C 72.13, H 4.20, N 5.12.

Part C: 3-(4-Carbethoxyphenyl)-N-phenylpropiolamide

A mixture of 1.00 g (3.77 mmol)3-(4-carboxyphenyl)-N-phenylpropiolamide, 1.00 g (excess) anhydrous sodium bicarbonate and 25 mL dry N,N-dimethylformamide was stirred at room temperature. Added was 1.95 g (excess) iodoethane and the mixture heated at 70°-80° C. for 3 hrs. The mixture was allowed to cool to room temperature and poured into 75 mL water. The resulting solid was filtered and recrystallized from ethanol/water to provide 0.99 g (3.37 mmol, 90%)3-(4-carbethoxyphenyl)-N-phenylpropiolamide as a pale, yellow powder, mp=114°-115° C. NMR ($CDCl_3$/TMS): 1.40 (t, 3H), 4.39 (q, 2H), 7.16 (t, 1H), 7.36 (t, 2H), 7.60 (d, 4H), 7.90 (s, 1H), 8.03 (d, 2H)). IR (KBr): 3292, 2210, 1692, 1660. High resolution mass spectrum: Calculated; 294.113019. Measured; 294.112376.

Part D: S-(1-(4-Carbethoxyphenyl)-2-(phenylcarbamoyl)vinyl) isothiuronium-p-toluenesulfonate A mixture of 0.85 g (2.90 mmol)3-(4-carbethoxyphenyl)-N-phenylpropiolamide, 0.22 g (2.90 mmol) thiourea, 0.55 g (2.90 mmol) p-toluenesulfonic acid monohydrate and 40 mL absolute ethanol was stirred at reflux for 3 hrs. The reaction was allowed to cool to room temperature and 100 mL diethyl ether was added. The resulting solid was filtered and suction dried to provide 1.24 g (2.29 mmol, 79%) S-(1-(4-carboxyphenyl)-2-(phenylcarbamoyl) vinyl)isothiuronium-p-toluenesulfonate as a pale, yellow powder, mp=200°-201° C. NMR ($d_6$-DMSO/TMS): 1.32 (t, 3H), 2.29 (s, 3H), 4.33 (q, 2H), 7.03-7.13 (m, 4H), 7.29 (t, 2H), 7.46-7.52 (m, 4H), 7.65 (d, 2H), 7.96 (d, 2H)9.18 (s, 2H), 9.36 (s, 2H), 10.34 (s, 1H). IR (KBr): 3280, 3122, 1718, 1668. Anal. calcd. for $C_{26}H_{27}N_3O_6S_2$: C 57.66, H 5.02, N 7.76, S 11.84; Found: C 57.46, H 5.03, N 7.62, S 11.97.

Part E: 3-(4-Carboxyphenyl)-3-mercapto-N-phenylpropenamide

A mixture of 1.15 g (2.12 mmol) S-(1-(4-carbethoxyphenyl)-2-(phenylcarbamoyl)vinyl) isothiuronium-p-toluenesulfonate 0.54 g (6.36 mmol) of 50% aqueous sodium hydroxide and 30 mL of 50% aqueous ethanol was stirred at reflux for 3 hrs. The mixture was allowed to cool to room temperature and added was 100 mL water. The mixture was washed with three 100 mL portions of diethyl ether and the aqueous layer was cooled in an ice bath. The solution was acidified to pH 3 with concentrated hydrochloric acid. The resulting solid was filtered and recrystallized from ethanol/water to provide 0.28 g (0.93 mmol, 44%) 3-(4-carboxyphenyl)-3-mercapto-N-phenylpropenamide as a pale, yellow powder, mp=210°-212° C. (d). NMR ($d_6$-DMSO/TMS): 6.58 (s, 1H), 7.10-8.03 (m, 12H). IR (KBr): 3286, 1684, 1640. Mass spectrum (CI): M/z=300 $(M+H)^+$.

Part F: 5-(4-Carboxyphenyl)-N-phenyl-4-isothiazolin-3-one

A mixture of 0.30 g (1.00 mmol)3-(4-carboxyphenyl)-3-mercapto-N-phenylpropenamide and 50 mL methylene chloride was stirred at room temperature. Added was 0.25 g (1.00 mmol) iodine followed by 0.2 mL (excess) triethylamine and the mixture stirred for one hour. Solvent was evaporated and 250 mL ethyl acetate added. The mixture was washed with three 100 mL portions of water. The organic layer was dried, filtered and solvent was evaporated from the filtrate. The resulting solid was triturated in absolute ethanol and filtered to dryness to provide 0.16 g (0.54 mmol, 54%)5-(4-carboxyphenyl)-N-phenyl-4-isothiazolin-3-one as a pale, yellow powder, mp=260-261° C. NMR ($d_6$-DMSO/TMS): 7.08 (s, 1H), 7.39-8.07 (m, 9H), 13.30 (bs, 1H). IR (KBr): 1678, 1652. Mass spectrum (CI): M/z=298.0 $(M+H)^+$.

EXAMPLE 10

Compound of Formula (I) in which $R^1$, $R^2$, $R^3$ and $R^4$=H and $R^5$, $Ar^1$ and $Ar^2$=phenyl Part A: Phenylacetanilide A mixture of 5.84 g (37.81 mmol) phenylacetyl chloride and 50 mL benzene was stirred at 0° C. A solution of 3.52 g (2.0 equivs.) aniline and 50 mL benzene was added dropwise. After addition was complete, the mixture was allowed to warm to room temperature and stirred for 3 hrs. The mixture was poured into 100 mL water and was extracted with 3×100 mL ethyl acetate. The organic layers were combined and washed sequentially with 100 mL portions of 5% aqueous hydrochloric acid, water, saturated sodium carbonate and water. The organic layer was dried, filtered and solvent was removed from the filtrate to provide 5.24 g (24.80 mmol, 65%) phenylacetanilide as a tan solid, mp=114°-116° C. NMR ($CDCl_3$/TMS): 3.73 (s, 2H), 7.08 (t, 1H), 7.18 (bs, 1H), 7.25-7.43 (m, 9H). Mass spectrum Part B: 2,3,N-triphenyl-3-mercaptopropenamide A mixture of 1.27 g (6.02 mmol) phenylacetanilide and 20 mL tetrahydrofuran was stirred at 0° C. Lithium diisopropylamide (4.4 mL of 1.5M in cyclohexane, 1.1 equivs.) was added dropwise and the solution stirred 15 mins. followed by stirring at room temperature for 15 mins. The mixture was then cooled to 0° C. and 1.00 g (6.02 mmol) O-ethylthiobenzoate (S. O. Lawesson, et. al., *Bull. Soc. Chim. Belg.* 87 (4), 293 (1978)) was added dropwise in 10 mL tetrahydrofuran. After addition was complete, the ice bath was removed and the solution stirred 30 mins. followed by stirring at reflux for 48 hrs. The solution was allowed to cool to room temperature and poured into 50 mL water. The aqueous layer was acidified with concentrated hydrochloric acid to yield a reddish-orange solid. The solid was recrystallized from absolute ethanol to provide 0.16 mg (0.48 mmol, 8%) 2,3,N-triphenyl-3-mercaptopropenamide as a pale, yellow solid, mp=144°-146° C.(d). NMR ($CDCl_3$/TMS): 5.20 (s, 1H), 7.07-7.41 (m, 16H). IR (KBr): 3400, 3302, 1658. Mass spectrum (CI); M/z=332 (M+H)+. Anal. calcd. for $C_{21}H_{17}NOS$: C 76.10, H 5.17, N 4.23, S 9.67; Found: C 75.94, H 5.10, N 4.16, S 9.83.

part C: 4,5,N-Triphenyl-4-isothiazolin-3-one

A mixture of 150 mg (0.450 mmol) 2,3,N-triphenyl-3-mercaptopropenamide and 25 mL methylene chloride was stirred at room temperature. Added was 115 mg (1 equiv.) of iodine followed by 116 mg (1 equiv.) of triethylamine and the mixture stirred for one hour. Solvent was evaporated and 50 mL ethyl acetate added and the mixture poured into 50 mL water. The organic layer was separated and washed with three 50 mL portions of water. The organic layer was dried, filtered and solvent was evaporated from the filtrate. The resulting solid was recrystallized from ethanol/water to provide 108 mg (0.327 mmol, 73%) 4,5,N-triphenyl-4-isothiazolin-3-one as a tan solid, mp=175°-176° C. NMR ($CDCl_3$/TMS): 7.30-7.72 (m, 15H). IR (KBr): 1656. Mass spectrum (CI): M/z=330 (M+H)+. Anal. calcd. for $C_{21}H_{15}NOS$: C 76.57, H 4.59, N 4.25, S 9.73; Found: C 76.25, H 4.40, N 4.19, S 9.81.

TABLE OF EXAMPLES

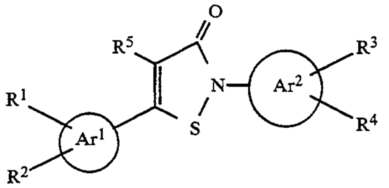

(I)

| Examp No. | $R^1$ | $R^2$ | $R^3$ | $R^4$ | $R^5$ | $Ar^1$ | $Ar^2$ | M.P. (°C.) |
|---|---|---|---|---|---|---|---|---|
| 1 | H | H | 4-$CH_3$ | H | H | Ph | Ph | 110-112 |
| 2 | H | H | H | H | Br | Ph | Ph | 114-117 |
| 3 | H | H | 4-$CO_2H$ | H | H | Ph | Ph | 238-240 |
| 4 | H | H | 4-$CO_2Et$ | H | H | Ph | Ph | 134-135 |
| 5 | H | H | 4-$CONH_2$ | H | H | Ph | Ph | 219-220 |
| 6 | H | H | 2-$NH_2$ | H | H | Ph | Ph | 145-146 |
| 7 | H | H | 4-$N(SO_2CF_3)_2$ | H | H | Ph | Ph | 184-186.5 |
| 8 | H | H | H | H | H | Ph | 2-benzothiazolyl | 201-202 |
| 9 | 4-$CO_2H$ | H | H | H | H | Ph | Ph | 260-261 |
| 10 | H | H | H | H | H | Ph | Ph | 175-176 |
| 11 | 2-Cl | H | H | H | H | Ph | Ph | 114-115 |
| 12 | 2-$OCH_3$ | H | H | H | H | Ph | Ph | 124-126 |
| 13 | H | H | 4-Cl | H | H | Ph | Ph | 134-135 |
| 14 | H | H | 4-$OCH_3$ | H | H | Ph | Ph | 121-123 |
| 15 | H | H | 4-$CF_3$ | H | H | Ph | Ph | 162-164 |
| 16 | H | H | 4-$NO_2$ | H | H | Ph | Ph | 207-210 |
| 17 | H | H | 2-$CH_3$ | 4-$NO_2$ | H | Ph | Ph | 165-168 |
| 18 | H | H | 4-CN | H | H | Ph | Ph | 190-193 |
| 19 | H | H | 3-Cl | H | H | Ph | Ph | 109-111 |
| 20 | H | H | 3-$OCH_3$ | H | H | Ph | Ph | 76-77 |
| 21 | H | H | 3-$CF_3$ | H | H | Ph | Ph | 112-113 |
| 22 | H | H | 2-$CH_3$ | H | H | Ph | Ph | 114-116 |
| 23 | H | H | 2-Cl | H | H | Ph | Ph | 122-124 |
| 24 | H | H | 2-$OCH_3$ | H | H | Ph | Ph | 147-150 |
| 25 | H | H | 2-$CF_3$ | H | H | Ph | Ph | 149-150 |
| 26 | H | H | 2-$NO_2$ | H | H | Ph | Ph | 190-192 |
| 27 | H | H | 4-Cl | H | H | Ph | Ph | 170-172 |
| 28 | 4-Cl | H | H | H | H | Ph | Ph | 138-139 |
| 29 | 3-Cl | H | H | H | H | Ph | Ph | 107-108 |
| 30 | 4-$OCH_3$ | H | H | H | H | Ph | Ph | 170-172 |
| 31 | 3-$OCH_3$ | H | H | H | H | Ph | Ph | 109-110 |
| 32 | 4-$CF_3$ | H | H | H | H | Ph | Ph | 179-180 |
| 33 | 3-$CF_3$ | H | H | H | H | Ph | Ph | 110-112 |

-continued

TABLE OF EXAMPLES

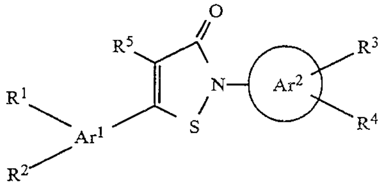

(I)

| Examp No. | $R^1$ | $R^2$ | $R^3$ | $R^4$ | $R^5$ | $Ar^1$ | $Ar^2$ | M.P. (°C.) |
|---|---|---|---|---|---|---|---|---|
| 34 | 2-$CF_3$ | H | H | H | H | Ph | Ph | 112–113 |
| 35 | H | H | 3-$CO_2H$ | H | H | Ph | Ph | 263–265 |
| 36 | H | H | 2-$CO_2H$ | H | H | Ph | Ph | 228–230 |
| 37 | H | H | 3-$CO_2CH_2CH_3$ | H | H | Ph | Ph | 96–98 |
| 38 | H | H | 2-$CO_2CH_2CH_3$ | H | H | Ph | Ph | 143–145 |
| 39 | H | H | 4-$NH_2$ | H | H | Ph | Ph | 163–166 |
| 40 | H | H | 2-$CH_3$ | 4-$NH_2$ | H | Ph | Ph | 180–183 |
| 41 | H | H | H | H | H | Ph | 2-thiazolyl | 136–137 |
| 42 | H | H | 4-F | H | H | Ph | Ph | |
| 43 | H | H | 4-Br | H | H | Ph | Ph | |
| 44 | H | H | 4-I | H | H | Ph | Ph | |
| 45 | 4-F | H | H | H | H | Ph | Ph | |
| 46 | 4-Br | H | H | H | H | Ph | Ph | |
| 47 | 4-I | H | H | H | H | Ph | Ph | |
| 48 | H | H | 3-$NHCH_3$ | H | H | Ph | Ph | |
| 49 | H | H | 3-$N(CH_3)_2$ | H | H | Ph | Ph | |
| 50 | 3-$N(CH_3)_2$ | H | H | H | H | Ph | Ph | |
| 51 | H | H | 4-$N(SO_2CH_3)_2$ | H | H | Ph | Ph | |
| 52 | 4-$N(SO_2CH_3)_2$ | H | H | H | H | Ph | Ph | |
| 53 | H | H | H | H | H | Ph | Ph | |
| 54 | 2-$COCH_3$ | H | 4-$CONCH_3$ | H | H | Ph | Ph | |
| 55 | H | H | H | H | H | Ph | Ph | |
| 56 | 2-$COCH_3$ | H | 4-$CON(CH_3)_2$ | H | H | Ph | Ph | |
| 57 | H | H | H | H | H | Ph | Ph | |
| 58 | H | H | 3-OH | H | H | Ph | Ph | |
| 59 | 3-OH | H | H | H | H | Ph | Ph | |
| 60 | H | H | 3-$COCH_3$ | H | H | Ph | Ph | |
| 61 | 4-$COCH_3$ | H | H | H | H | Ph | Ph | |
| 62 | H | H | 4-(5-tetrazolyl) | H | H | Ph | Ph | |
| 63 | 4-(5-tetrazolyl) | H | H | H | H | Ph | Ph | |
| 64 | H | H | 4-CONHOH | H | H | Ph | Ph | |
| 65 | 4-CONHOH | H | H | H | H | Ph | Ph | |
| 66 | H | H | 3-$SCH_3$ | H | H | Ph | Ph | |
| 67 | 3-$SCH_3$ | H | H | H | H | Ph | Ph | |
| 68 | H | H | 3-$SOCH_3$ | H | H | Ph | Ph | |
| 69 | 3-$SOCH_3$ | H | H | H | R | Ph | Ph | |
| 70 | H | H | 3-$SO_2CH_3$ | H | H | Ph | Ph | |
| 71 | 3-$SO_2CH_3$ | H | H | H | H | Ph | Ph | |
| 72 | H | H | 3-$N(CH_3)CO_2CH_3$ | H | H | Ph | Ph | |
| 73 | 3-$N(CH_3)CO_2—CH_3$ | H | H | H | H | Ph | Ph | |
| 74 | H | H | 3-$N(CH_3)COCH_3$ | H | H | Ph | Ph | |
| 75 | 3-$N(CH_3)COCH_3$ | H | H | H | H | Ph | Ph | |
| 76 | H | H | 3-$OCON—(CH_3)_2$ | H | H | Ph | Ph | |
| 77 | 3-$OCON—(CH_3)_2$ | H | H | H | H | Ph | Ph | |
| 78 | H | H | 4-$(C═S)N(CH_3)_2$ | H | H | Ph | Ph | |
| 79 | 4-$(C═S)N(CH_3)_2$ | H | H | H | H | Ph | Ph | |
| 80 | H | H | 4-$SO_3H$ | H | H | Ph | Ph | |
| 81 | 4-$SO_3H$ | H | H | H | H | Ph | Ph | |
| 82 | R | H | 4-$PO_3H$ | H | H | Ph | Ph | |
| 83 | 4-$PO_3H$ | H | H | H | H | Ph | Ph | |
| 84 | H | H | 4-$SO_2N—(CH_3)_2$ | H | H | Ph | Ph | |
| 85 | 4-$SO_2N—(CH_3)_2$ | H | H | H | H | Ph | Ph | |
| 86 | H | H | H | H | $CH_3$ | Ph | Ph | |
| 87 | H | H | H | H | $COCH_3$ | Ph | Ph | |
| 88 | H | H | H | H | CN | Ph | Ph | |
| 89 | H | H | H | H | $CO_2CH_3$ | Ph | Ph | |
| 90 | H | H | H | H | $CONH_2$ | Ph | Ph | |
| 91 | H | H | H | H | $SCH_3$ | Ph | Ph | |
| 92 | H | H | H | H | $OCH_3$ | Ph | Ph | |

The compounds are efficacious in an in vitro cytokine-induced cartilage degradationassay (Arner EC and Pratta MA 1989. Arthritis Rheum 32:288–297). The activity of these compounds in blocking IL-lb-induced proteoglycan breakdown in bovine nasal cartilage was assessed.

Bovine nasal cartilage was incubated in Dulbecco's 10 modified Eagle's Medium (DMEM) containing 5% FCS and antibiotics at 37° C. in an atmosphere of 95% air and 5% CO2 for 40 hours in the absence or presence of IL-lb (500 ng/ml), with or without compound. Compounds were dissolved in DMSO (10-2M) and further diluted with 15 medial to the required concentration and were included throughout the culture period. At the end of incubation, media were removed and assayed proteoglycan breakdown products using the 1,9 dimethylmethylene blue assay for glycosaminoglycans. Compounds were evaluated for the ability to block the stimulated release of proteoglycan in response to IL-l.

| | Bovine Nasal Septum Cartilage Degradation Assay | |
|---|---|---|
| EX. No. | (IC50 μM OR | % Inhibition at 30 μM) |
| 1 | 13.2 | |
| 2 | | 38 |
| 3 | | 19 |
| 4 | 8.3 | |
| 5 | | 42 |
| 6 | | 19 |
| 7 | | 48 |
| 8 | 15.0 | |
| 9 | | 18 |
| 10 | 43.5 | |
| 11 | 11.2 | |
| 12 | 34.5 | |
| 13 | 14.8 | |
| 14 | | 85 |
| 15 | 7.2 | |
| 16 | 31 | |
| 17 | 14 | |
| 18 | 7.8 | |
| 19 | 11.3 | |
| 20 | 19.0 | |
| 21 | 7.0 | |
| 22 | | 52 |
| 23 | | 33 |
| 24 | | 61 |
| 25 | | 25 |
| 26 | | 43 |
| 27 | 25.0 | |
| 28 | 14.8 | |
| 29 | 18.5 | |
| 30 | | 37 |
| 31 | | 26.6 |
| 32 | | 25 |
| 33 | 14.0 | |
| 34 | 7.2 | |
| 35 | | 13 |
| 36 | | 26 |
| 37 | 7.8 | |
| 38 | 12.0 | |
| 39 | | 32 |
| 40 | | 14 |

Dosage and Formulation

Compounds may be administered by any means that enables the active agent to reach the agent's site of action in the body of a mammal. They can be administered by any of the conventional means available for administration of pharmaceuticals, either as individual therapeutic agents or in combinations with other therapeutic agents. They can be administered alone, but are generally administered with a pharmaceutical carrier selected on the basis of the chosen route of administration and standard pharmaceutical practice.

The dosage administration will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually, a daily dosage of active ingredient can be about 0.1 to 100 milligrams per kilogram of body weight. Ordinarily 0.5 to 50, and preferably 1 to 10 milligrams per kilogram per day given in divided doses 1 to 6 times a day or in sustained release form is effective to obtain desired results.

Dosage forms (compositions) suitable for internal administration generally contain from about 1 milligram to about 500 milligrams of active ingredient per unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms, by inhalation in the form of a nasal spray or lung inhaler.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose) and related sugar solutions, and glycols such as propylene glycol or polyethylene glycols are suitable carriers for parenteral solutions. Solutions for parenteral administration contain the active ingredient, and, if necessary, suitable stabilizing agents, and/or buffer substances. Antioxidants such as sodium bisulfite, sodium sulfite, or ascorbic acid either alone or in combination are frequently suitable stabilizing agents. Also used are citric acid and its salts and sodium EDTA. In addition, parenteral solutions can contain preservatives, such as benzalkonium chloride, methyl and/or phenyl parabens, and chlorobutanol.

Suitable pharmaceutical carriers are described in "*Remington's Pharmaceutical Sciences,*" Mack Publishing, a standard reference text in this field.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed is:

1. A method of treating inflammation in a patient in need of such treatment said method comprising administering to the patient an anti-inflammatory effective amount of a compound of the Formula (I) wherein:

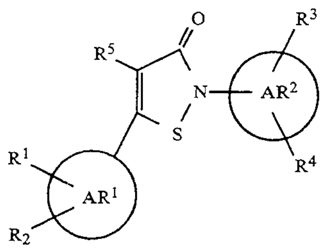

(I)

$Ar^1$ and $Ar^2$ are each independently a $C_5$ to $C_{10}$ saturated or unsaturated carbocyclic ring;

$R^1$, $R^2$, $R^3$, and $R^4$ each independently are: H, straight or branched alkyl chain of 1 to 6 carbon atoms, substituted with 0–3 R8, alkenyl of 2–4 carbon atoms, alkynyl of 2 to 4 carbon atoms, F, Cl, Br, I, OH, $OR^6$, $CO_2H$, $OCOR_6$, $OCO_2R^6$, $OCON(R^6)_2$, $NO_2$, $NR^6R^7$, $NHR^7$, $NR^6C(=O)$ $R^6$, CF3, $NR^6C(=O)$ $OR^6$, $N(C(=S)R^6)2$, $NR^6C(+O)$ N $(R^6)2$, $NR^6SOR^6$, $N(SO_2R^6)_2$, $N(SO_2CF_3)_2$, $SR^6$, $S(O)R^6$, $SO_2R^7$, $SO_3H$, $SO_2N(R^6)2$, $SO_2NR^6R^7$, $COR^6$, $CO_2R^6$, $CON(R^6)_2$ $C(=S)$ $NHR^6$, $C(=S)$ $N(R^6)_2$, $CONR^6OR^6$, CN, $CONH_2$, $CONHR^6$, $R^6CO_2R^7$, tetrazolyl, or hydroxamic acid;

$R^5$ is H, Br, $OR^6$, $SR^6$, $COR^6$, CO($R^1$–$R^4$ substituted $Ar^1$), $R^6$, $CO_2R^6$, $CO_2H$, $CONH_2$, $CONHR^6$, $CON(R^6)_2$, CONH ($R^1$–$R^4$ substituted $Ar^1$), CON ($R^1$–$R^4$ substituted) $Ar^1)_2$, CN or $R^1$–$R^4$ substituted $Ar^1$;

$R^6$ is straight or branched alkyl chain of 1 to 4 carbon atoms, alkenyl of 3–4 carbon atoms or alkynyl of 3–4 carbon atoms, and;

$R^7$ is H, straight or branched alkyl chain of 1 to 4 carbon atoms, alkenyl of 2–4 carbon atoms, or $COR^6$; and, $R^8$ is: H, straight or branched alkyl chain of 1 to 6 carbons substituted with 0–3 $R^6$alkenyl of 2–4 carbon atoms, alkynyl of 2–4 carbon atoms, halo, OH, $OR^6$, $CO_2H$, $OCOR^6$, $OCO_2R^6$, OCON $(R^6)_2$, $NO_2$, $NR^6R^7$, $NHR^7$, $NR^6C$ (=) $R^6$, $NR^6C(=O)OR^6$, $N(C(=S)R^6)_2$, $NR6C(=O)N(R^6)2$, $NR^6SO2R^6$, $N(SO_2R^6)2$, $SR^6$, $S(O)R^6$, $SO_2R^7$, $SO_3H$, $SO_2N(R^6)_2$, $SO2NR^6R^7$, $COR^6$, $CO_2R^6$, CON $(R^6)_2$, $C(=S)$ $NHR^6$, $C(=S)$ N $(R^6)2$, $CONR^6OR^6$, CN, $CONH_2$, $CONHR^6$, $R^6CO_2$, tetrazolyl, and hydroxamic acid; with the proviso that $R^1$–$R^5$ may not simultaneously be H when $Ar^1$ and $Ar^2$ are each phenyl; or a pharmaceutically acceptable salt thereof.

2. The method claim 1 wherein in the compound of Formula (I) $Ar^1$ is phenyl;

$Ar^2$ is phenyl:

$R^2$ is H; $R^3$ is H, OH, $CH_3$, $CO_2H$, $CO_2C_2H_5$, $CONH_2$, $NH_2$, $N(SO_2CF_3)_2$, halo, $OCH_3$, $CF_3$, $NO_2$, CN, $NHCH_3$, $N(CH_3)_2$, $N(SO_2CH_3)_2$, $CONHCH_3$, CON $(CH_3)_2$, $COCH_3$, CONHOH, $SCH_3$, $SOCH_3$, $SO_2CH_3$, $N(CH_3)$ $CO_2CH_3$ or tetrazolyl;

$R^4$ is H, NO2; and $R^5$ is H or halo.

3. The method of claim 2 wherein in the compound of Formula (I) :

$Ar^2$ is phenyl;

$R^1$ is H, halo, OH, $CO_2H$, $OCH_3$, or $CF_3$; and $R_3$ is H, OH, $CH_3$, $CO_2H$, $CO_2CH_5$, $CONH_2$, $NH_2$, N $(SO_2CF_3)_2$, halo, $OCH_3$, $CF_3$, $NO_2$, CN.

4. The method of claim 3 wherein in the compound of Formula (I):

$Ar^1$ and $Ar^2$ are phenyl; and $R^4$ is 4-$CO_2C_2H_5$, 4-CN, 4-$CF_3$ or 4-C1.

* * * * *